(12) United States Patent
Matsuki (10) Patent No.: US 11,636,378 B2
(45) Date of Patent: Apr. 25, 2023

(54) INFORMATION PROCESSING APPARATUS, INFORMATION PROCESSING METHOD, AND INFORMATION PROCESSING SYSTEM

(71) Applicant: CANON KABUSHIKI KAISHA, Tokyo (JP)

(72) Inventor: Naoki Matsuki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1247 days.

(21) Appl. No.: 16/113,861

(22) Filed: Aug. 27, 2018

(65) Prior Publication Data

US 2019/0065996 A1    Feb. 28, 2019

(30) Foreign Application Priority Data

Aug. 31, 2017 (JP) .............................. JP2017-167258

(51) Int. Cl.

| | |
|---|---|
| *G06F 16/20* | (2019.01) |
| *G06N 20/00* | (2019.01) |
| *G06F 16/28* | (2019.01) |
| *G06F 16/35* | (2019.01) |
| *G16H 40/20* | (2018.01) |
| *G16H 50/20* | (2018.01) |
| *G06N 3/08* | (2023.01) |
| *G06N 3/04* | (2023.01) |

(Continued)

(52) U.S. Cl.
CPC ............ *G06N 20/00* (2019.01); *G06F 16/11* (2019.01); *G06F 16/21* (2019.01); *G06F 16/24578* (2019.01); *G06F 16/285* (2019.01); *G06F 16/3323* (2019.01); *G06F 16/35* (2019.01); *G06N 3/0454* (2013.01); *G06N 3/08* (2013.01); *G16H 40/20* (2018.01); *G16H 50/20* (2018.01)

(58) Field of Classification Search
None
See application file for complete search history.

(56) References Cited

U.S. PATENT DOCUMENTS

| | | | | |
|---|---|---|---|---|
| 7,577,709 B1 * | 8/2009 | Kolcz | .................. | H04L 51/212 |
| | | | | 706/20 |
| 9,189,746 B2 * | 11/2015 | Zhu | ......................... | G06F 21/31 |

(Continued)

FOREIGN PATENT DOCUMENTS

| | | |
|---|---|---|
| CN | 102521227 A | 6/2012 |
| CN | 104573359 A | 4/2015 |

(Continued)

*Primary Examiner* — Belix M Ortiz Ditren
(74) *Attorney, Agent, or Firm* — Canon U.S.A., Inc. IP Division (57) ABSTRACT

An information processing apparatus includes an itemized reliability level calculation unit configured to calculate a first reliability level, wherein the first reliability level is a reliability level of classification target data, and a second reliability level, wherein the second reliability level is a reliability level of a label associated with the classification target data, a learning data reliability level calculation unit configured to calculate a learning data reliability level of learning data including the classification target data and the label based on the first reliability level and the second reliability level, and a classification model learning unit configured to formulate a classification model for giving a label to desired classification target data based on plural pieces of learning data and learning data reliability levels.

9 Claims, 8 Drawing Sheets

(51) Int. Cl.
*G06F 16/11* (2019.01)
*G06F 16/21* (2019.01)
*G06F 16/2457* (2019.01)
*G06F 16/332* (2019.01)

(56) References Cited

U.S. PATENT DOCUMENTS

| | | | |
|---|---|---|---|
| 9,704,106 B2 * | 7/2017 | Welinder | G06F 16/24573 |
| 2002/0161763 A1 * | 10/2002 | Ye | G06F 21/55 |
| 2015/0120639 A1 * | 4/2015 | Shin | G06K 9/6221 |
| | | | 706/46 |

FOREIGN PATENT DOCUMENTS

| | | |
|---|---|---|
| CN | 105359166 A | 2/2016 |
| CN | 105426826 A | 3/2016 |
| CN | 105612514 A | 5/2016 |
| CN | 105975980 A | 9/2016 |
| CN | 106485528 A | 3/2017 |
| JP | 2009-282686 A | 12/2009 |
| JP | 2015-230570 A | 12/2015 |
| KR | 100723873 B1 | 5/2007 |

* cited by examiner

EXAMPLE OF MEDICAL IMAGE DATA

PATIENT ID: ID000X11
IMAGING DATE AND TIME: 2017/08/05 11:00
IMAGING EQUIPMENT: CT-X0123
IMAGING CONDITION: NO CONTRAST MEDIUM
PHOTOGRAPHER: SABURO KAWASAKI (TECHNICIAN)

ID: IMG0001

EXAMPLE OF RADIOGRAPHIC INTERPRETATION REPORT

PATIENT ID: ID000X11
CREATION DATE AND TIME: 2017/08/05 16:00
CREATOR: JIRO HIRAMA (RADIOGRAPHIC INTERPRETATION DOCTOR)

| ID | TYPE | CONTENTS | CREATOR | SOURCE LINK ID |
|---|---|---|---|---|
| 0001 | KEY IMAGE | ID: IMG0001 (LINK TO IMAGE) | | N/A |
| 0002 | ROI | ID: IMG0001 Pos = (25, 60, 20) Size = (40,40,40) | JIRO HIRAMA (RADIOGRAPHIC INTERPRETATION DOCTOR) | 0001 |
| 0003 | IMAGE-BASED FINDINGS | PRESENCE OF CALCIFICATION | JIRO HIRAMA (RADIOGRAPHIC INTERPRETATION DOCTOR) | 0002 |
| 0004 | IMAGE-BASED DIAGNOSIS | IMAGE-BASED DIAGNOSIS 2017/08/05 11:00 | JIRO HIRAMA (RADIOGRAPHIC INTERPRETATION DOCTOR) | 0003 |

⋮

EXAMPLE OF ELECTRONIC HEALTH RECORD

| TYPE | CONTENTS | CREATOR | CREATION DATE AND TIME |
|---|---|---|---|
| PATIENT ID | ID000X11 | SYSTEM | 2017/08/05 09:30 |
| PAST MEDICAL HISTORY | WITH HISTORY OF SMOKING NO HISTORY OF ILLNESS | TARO SHIMOMARUKO (CLINICIAN) | 2017/08/05 09:40 |
| SYMPTOMS | CHEST PAIN | TARO SHIMOMARUKO (CLINICIAN) | 2017/08/05 09:40 |
| TEST REQUEST | IMAGE-BASED DIAGNOSIS 2017/08/05 11:00 | TARO SHIMOMARUKO (CLINICIAN) | 2017/08/05 09:50 |
| TEST RESULT | (LINK TO RADIOGRAPHIC INTERPRETATION REPORT) | SYSTEM | 2017/08/05 16:00 |
| DIAGNOSIS | SUSPICION OF LUNG CANCER | TARO SHIMOMARUKO (CLINICIAN) | 2017/08/05 16:10 |
| TEST REQUEST | PATHOLOGICAL DIAGNOSIS 2017/08/06 10:00 | TARO SHIMOMARUKO (CLINICIAN) | 2017/08/05 16:40 |
| TEST RESULT | (LINK TO PATHOLOGICAL REPORT) | SYSTEM | 2017/08/06 12:20 |
| DIAGNOSIS | LUNG CANCER (DEFINITIVE DIAGNOSIS) | TARO SHIMOMARUKO (CLINICIAN) | 2017/08/06 12:40 |

| | LESION IMAGE | (ASSOCIATION) | DIAGNOSIS |
|---|---|---|---|
| DATA |  | — | METASTASIS TO THE LUNG |
| CREATOR | AI | RESIDENT | CLINICIAN |

FIG.4B

| | MEDICAL IMAGE | LESION IMAGE | (ASSOCIATION) | DIAGNOSIS |
|---|---|---|---|---|
| DATA | | | — | METASTASIS TO THE LUNG |
| CREATOR | CT-0001 | AI | RESIDENT | CLINICIAN |

FIG.4C

| | LESION IMAGE | (ASSOCIATION) | DIAGNOSIS |
|---|---|---|---|
| DATA |  | — | METASTASIS TO THE LUNG |
| CREATOR 1 | CT-0001 | RESIDENT | PATHOLOGIST |
| CREATOR 2 | RADIOGRAPHIC INTERPRETATION DOCTOR | | CLINICIAN |
| CREATOR 3 | AI | | |

FIG.6A
EXAMPLE OF RELIABILITY LEVEL
BASED ON CREATOR OF LESION IMAGE

| CREATOR | RELIABILITY LEVEL |
|---|---|
| RADIOGRAPHIC INTERPRETATION DOCTOR | 1.0 |
| PATHOLOGIST | 0.9 |
| CLINICIAN | 0.6 |
| RADIOLOGICAL TECHNOLOGIST | 0.6 |
| RESIDENT | 0.2 |
| AI | 0.2 |

FIG.6B
EXAMPLE OF RELIABILITY LEVEL
BASED ON CREATOR OF DIAGNOSIS

| CREATOR | RELIABILITY LEVEL |
|---|---|
| CLINICIAN | 1.0 |
| PATHOLOGIST | 0.9 |
| RADIOGRAPHIC INTERPRETATION DOCTOR | 0.6 |
| RESIDENT | 0.4 |
| MEDICAL STUDENT | 0.2 |
| AI | 0.2 |

FIG.6C
EXAMPLE OF RELIABILITY LEVEL BASED ON CREATOR OF
RELATIONSHIP BETWEEN LESION IMAGE AND DIAGNOSIS

| CREATOR | RELIABILITY LEVEL |
|---|---|
| CLINICIAN | 1.0 |
| PATHOLOGIST | 0.9 |
| RADIOGRAPHIC INTERPRETATION DOCTOR | 0.6 |
| RESIDENT | 0.4 |
| MEDICAL STUDENT | 0.2 |
| AI | 0.2 |

FIG.8

INFORMATION PROCESSING APPARATUS, INFORMATION PROCESSING METHOD, AND INFORMATION PROCESSING SYSTEM

BACKGROUND

Field of the Disclosure

The present disclosure relates to an information processing apparatus, method, and system.

Description of the Related Art

In order to formulate a classification model for classifying desired data through machine learning, a great deal of learning data sets, each of which includes a set of classification target data and a correct label, are needed.

In the process of collecting lots of learning data, data having an incorrect label could be included, which decreases the accuracy the classification performed by the classification model d. Thus, a technique to evaluate the reliability level of the learning data and adjust the influence on the learning on the basis of the evaluation result is used. For example, Japanese Patent Application Laid-Open No. 2009-282686 and Japanese Patent Application Laid-Open No. 2015-230570 discuss a technique to evaluate the reliability level of learning data on the basis of information about the creator of the learning data and adjust the impact on the learning on the basis of the evaluation result.

However, in a case where a high level of expertise is needed, for example, when image-based diagnosis or pathological diagnosis is performed in the field of medicine, each individual item in learning data may be created by a different creator. In such a case, each item in the learning data has a different reliability level. Thus, the technique discussed in Japanese Patent Application Laid-Open No. 2009-282686 and Japanese Patent Application Laid-Open No. 2015-230570 has a problem in that the reliability level of the individual learning data cannot be evaluated accurately.

SUMMARY

The present disclosure is directed to providing an information processing apparatus, method, and system capable of accurately evaluating the reliability level of learning data even when each item in the learning data has a different reliability level.

In addition, the present disclosure is directed to providing an advantageous effect that can be achieved by the components as described in the following exemplary embodiments but cannot be achieved by conventional techniques.

An information processing apparatus according to an exemplary embodiment of the present invention includes an itemized reliability level calculation unit configured to calculate a first reliability level, wherein the first reliability level is a reliability level of classification target data, and a second reliability level, wherein the second reliability level is a reliability level of a label associated with the classification target data, a learning data reliability level calculation unit configured to calculate a learning data reliability level of learning data including the classification target data and the label based on the first reliability level and the second reliability level, and a classification model learning unit configured to formulate a classification model for giving a label to desired classification target data based on plural pieces learning data and learning data reliability levels.

Further features of the present invention will become apparent from the following description of exemplary embodiments with reference to the attached drawings

DESCRIPTION OF THE EMBODIMENTS

Exemplary embodiments of the present invention will be described below with reference to drawings.

A first exemplary embodiment will is described below. An information processing apparatus according to the first exemplary embodiment formulates a classifier for classifying lesion images into diagnoses of predetermined types. The information processing apparatus formulates the classifier by performing machine learning that uses learning data, which treat a lesion image as classification target data and a diagnosis as a correct label.

The first exemplary embodiment will be described by using a differential diagnosis of lung cancer as an example. In a differential diagnosis of lung cancer, a chest X-ray computed tomography (CT) image is captured as a medical image for radiographic interpretation of an abnormal shadow in a lung. Next, a radiographic interpretation doctor makes an image-based diagnosis, and a pathologist makes a pathological diagnosis. Finally, a clinician makes a definitive diagnosis. In the first exemplary embodiment, an image including an abnormal shadow is extracted from a medical image and is used as a lesion image, and a diagnosis name is determined to be one of the three categories of lung cancer (primary cancer), metastasis to the lung (metastatic cancer), and others as a classification.

Naturally, the present invention is not limited to what is described in the first exemplary embodiment. The following diagnoses, medical information, etc. are only examples to describe the steps of the processing performed by the information processing apparatus. For example, instead of a differential diagnosis of lung cancer, the present invention may be applied to a differential diagnosis of liver cancer or other diseases. In addition, instead of the medical image captured by a CT apparatus, a medical image captured by other imaging apparatuses (modalities) such as a magnetic resonance imaging (an MRI apparatus) or an ultrasound imaging apparatus (a US apparatus) may be used. In addition, the diagnosis name may not be determined to be one of, not just three categories of primary cancer, metastatic cancer, and others but may be classified into more specific categories, or different diagnose names may be added.

Hardware Configuration

Figure 8:
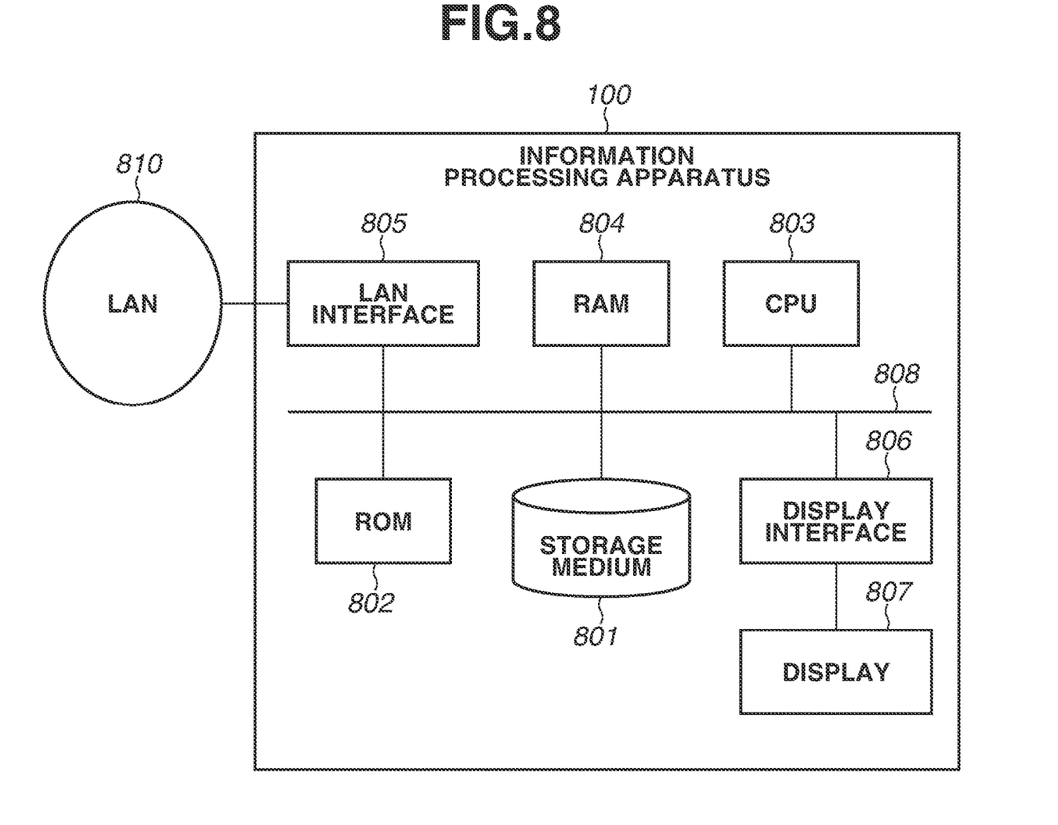
FIG. 8 illustrates an example of a hardware configuration of the information processing apparatus.

FIG. 8 illustrates a hardware configuration example of an information processing apparatus 100 according to the first exemplary embodiment. The hardware configuration in the first exemplary embodiment is only an example. The information processing apparatus 100 may have hardware components different from those illustrated in FIG. 8. In addition, it is only necessary that the information processing apparatus 100 has at least one hardware component illustrated in FIG. 8. Alternatively, the information processing apparatus 100 may have a plurality of each or any hardware component.

In FIG. 8, a storage medium 801 is a medium. such as a hard disk drive (HDD) that holds an operating system (OS) and a processing program, various kinds of information, and various kinds of databases for performing various processing according to the first exemplary embodiment. A read-only memory (ROM) 802 holds a program, such as a basic input/output system (BIOS) for initializing hardware components and starting the OS. A central processing unit (CPU) 803 performs arithmetic processing when the BIOS, the CS, or the processing program is executed. A random access memory (RAM) 804 temporarily holds information when the CPU 803 executes a program. A local area network (LAN) interface 805 is in conformity with a standard such as Institute of Electrical and Electronics Engineers (IEEE) 802.3ab and performs communication via a LAN 810. A display (display unit) 807 presents a display screen, and a display interface 806 converts screen information to be displayed on the display 807 into a signal and outputs the converted signal. Each block performs communication via an internal bus 808.

Functional Configuration

Figure 1:
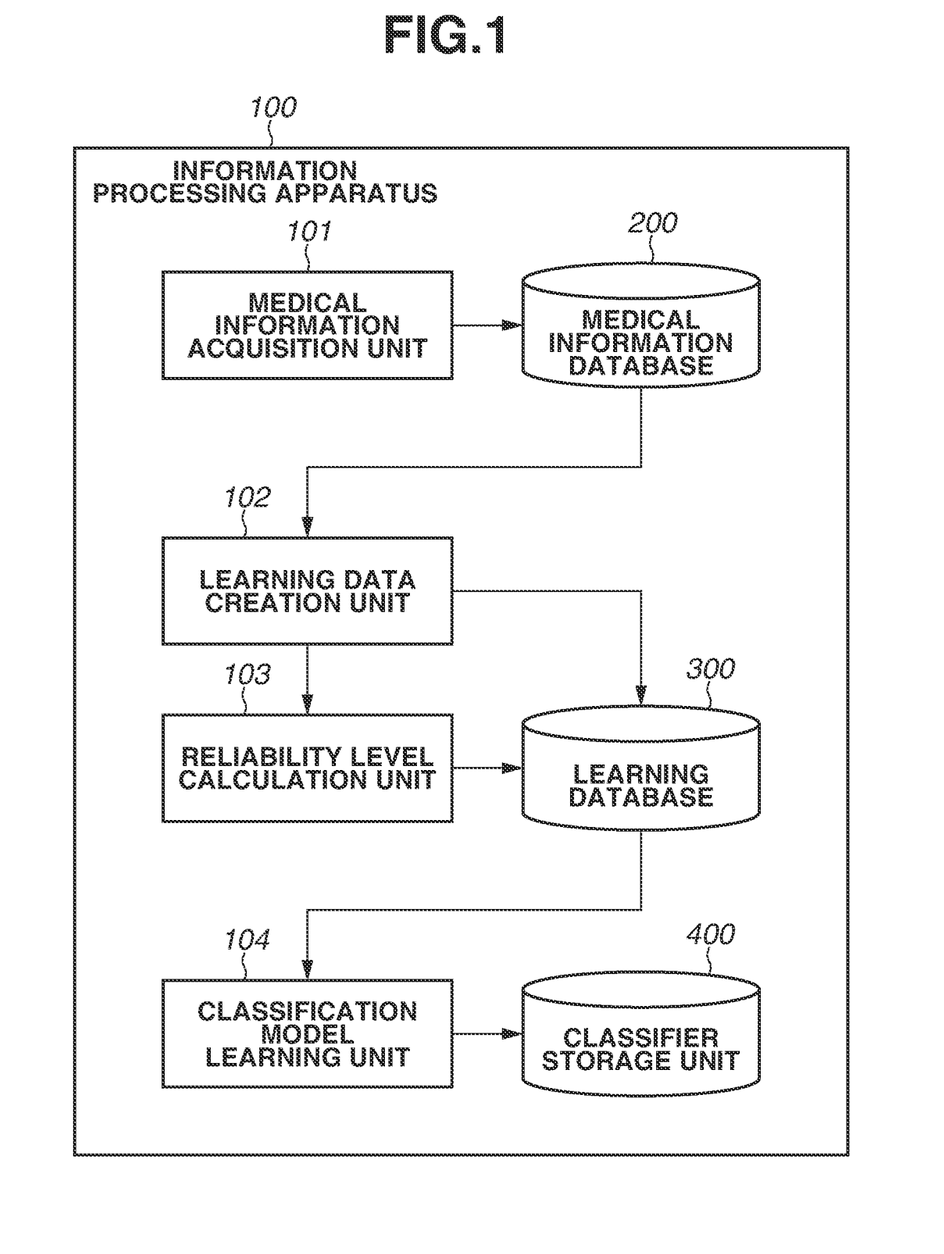
FIG. 1 illustrates an example of a functional configuration of an information processing apparatus.

FIG. 1 illustrates an example of a functional configuration of an information processing apparatus 100 according to the first exemplary embodiment. The each component of the information processing apparatus 100 functions in accordance with a computer program. For example, the functions of the individual components are realized by causing the CPU 803 to read a computer program stored in the ROM 802, the storage medium 801, or the like into the RAM 804 serving as a work area and to execute the read computer program. The functions of the components of the information processing apparatus 100 may partially or entirely be realized by using a dedicated circuit. The functions of the components of the CPU 803 may be partially realized by using a cloud computer.

For example, an arithmetic apparatus located at a place different from where the information processing apparatus 100 is located may communicably be connected to the information processing apparatus 100 via a network. In this case, the functions of the components of the information processing apparatus 100 or the CPU 803 may be realized by allowing the information processing apparatus 100 and the arithmetic apparatus to exchange data with each other.

A medical information acquisition unit 101 acquires medical information such as medical images, radiographic interpretation reports, and clinical information from a database (not illustrated) and stores the acquired medical information in a medical information database 200. The database (not illustrated) may be present inside a hospital or information made publicly available on a network outside a hospital. A configuration of the medical information will be described below with reference to FIG. 2.

A learning data creation unit 102 creates learning data on the basis of the information stored in the medical information database 200. The learning data created by the learning data creation unit 102 is stored in a learning database 300.

The method for creating the learning data will be described below with reference to FIG. 3.

A reliability level calculation unit 103 calculates the reliability level of the learning data created the learning data creation unit 102 and stores the calculated reliability level in the learning database 300. A method for calculating the reliability level of the learning data will be described below with reference to FIG. 3. More specifically, the reliability level calculation unit 103 is an example of an itemized reliability level calculation unit configured to calculate a first reliability level, which is a reliability level of classification target data, and a second reliability level, which is a reliability level of a label associated with the classification target data.

A classification model learning unit 104 formulates a classifier through machine learning by using the learning data stored in the learning database 300. The formulated classifier is stored in a classifier storage unit 400. More specifically, the classification model learning unit 104 is an example of a classification model learning unit configured to formulate a classification model for giving a label to desired classification target data on the basis of plural pieces of learning data and learning data reliability levels.

The processing of the medical information acquisition unit 101 is executed at regular intervals, e.g., once a day or once a month. In this way, information is added to the medical information database 200 or updated. When the addition or updating is performed, the processing in the learning data creation unit 102 and the reliability level calculation unit 103 is performed. In this way, new information is added to the learning database 300 or the information in the learning database 300 is updated. When this addition or updating is performed, the processing in the classification model learning unit 104 is performed, and the classifier is updated.

The processing in the medical information acquisition unit 101, the learning data creation unit 102, the reliability level calculation unit 103, and the classification model learning unit 104 may be performed at different timing from those described above. For example, regarding the learning data creation unit 102, some of the processing may be skipped. For example, the data of patient IDs, under which definitive diagnoses have already been registered from electronic health records, may not be updated.

Configuration of Medical Information

Figure 2:
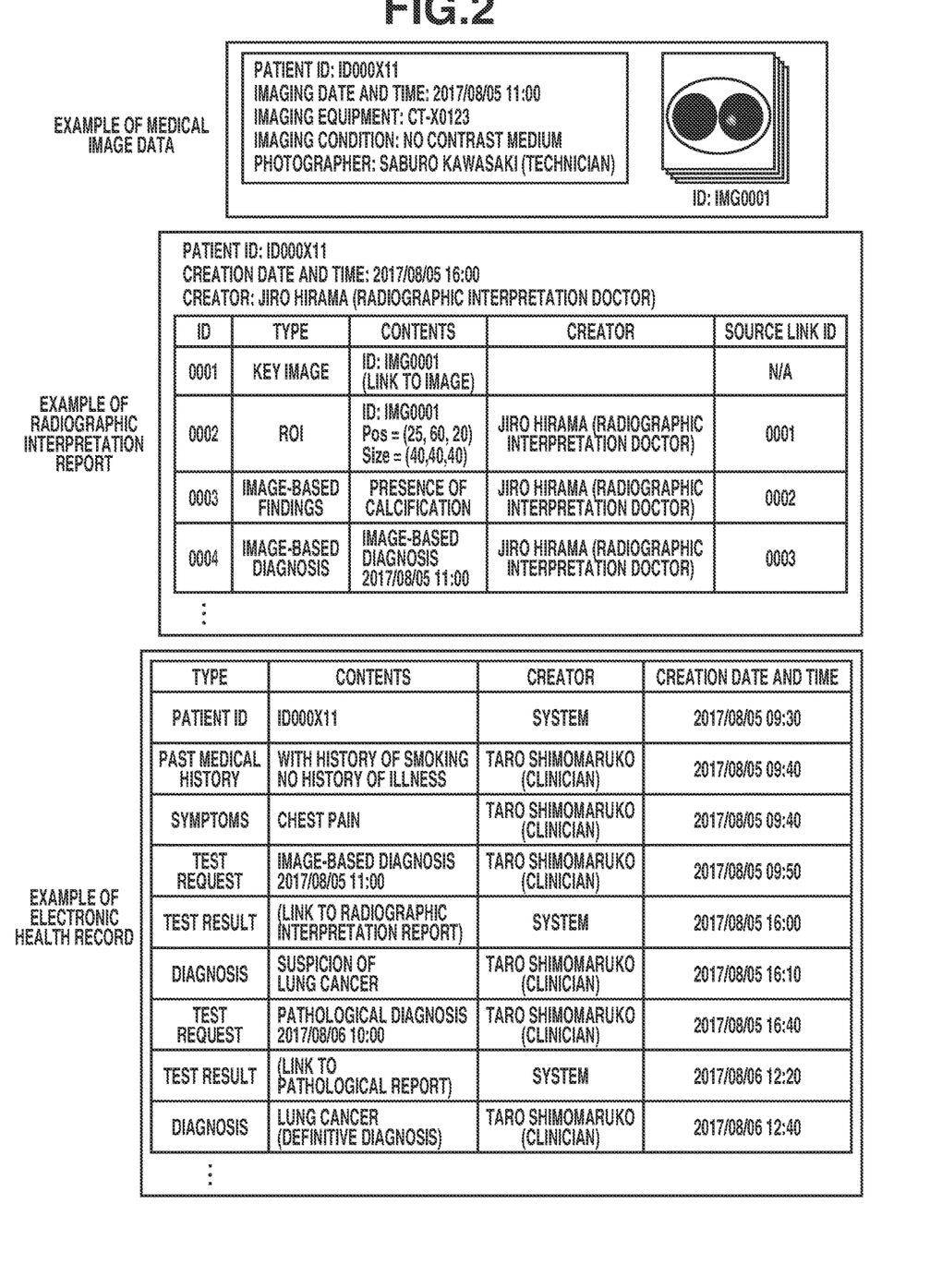
FIG. 2 illustrates an example of a configuration of medical information.

According to the first exemplary embodiment, the medical information database 200 holds the data of electronic health records, medical images, and radiographic interpretation reports in a table format as illustrated in FIG. 2.

For example, information about a patient ID, a past medical history, and a definitive diagnosis is registered in an electronic health record. In addition, information about a creator and a creation date and time are included in the registered information.

The patient ID, imaging equipment, an imaging condition, a creation (imaging) data and time, and information about an image such as a slice thickness are also registered in a medical image, in addition to image data.

in a radiographic interpretation report, the patient ID, the creator of the report, the creation date and time of the report, a key image, image-based findings, and an image-based diagnosis are registered. The key image is a snapshot of an image including an abnormal shadow and includes a link to a corresponding medical image and information about a region of interest (ROI) indicating the position and size of the abnormal shadow. The image-based findings are information indicating characteristics of the abnormal shadow, such as the size, shape, and concentration of the abnormal shadow. The individual image-based finding is created in association with an ROI on a one-on-one basis. The image-based diagnosis is a diagnostic name derived from. the image-based findings and is related to at least one image-based finding. Information about a creator and a source link ID is included in each of the key image, the image-based findings, and the image-based diagnosis. The key image, the image-based findings, and the image-based diagnosis are associated with each other, and the association is recognizable from the source link IDs. A plurality of key images, image-based findings, and image-based diagnoses may be registered in one radiographic interpretation report.

The relationship among each item of the information registered in an electronic health record, a medical image, and a radiographic interpretation report can be recognized for each patient and chronologically from the patient IDs and creation dates and times given to the above respective data.

While the data is stored in a table format in FIG. 2, the data may also be stored in a different format, for example, by using Extensible Markup Language (XML) representing an equivalent subject regarding the relationship among the information.

Alternatively, the data may be stored in a different format that does not explicitly represent the relationship among the information. In this case, when the data is used by the learning data creation unit 102, the data may be converted into the format illustrated in FIG. 2. For example, a radiographic interpretation report may be stored. In a format in which an image-based findings and a diagnosis are written by consecutive natural sentences. In this case, for example, natural language processing may be performed to recognize the relationship among the information.

The information to be stored. In the medical information database 200 may be anonymized in such a manner that the relationship among the information is maintained.

Method for Creating Learning Data

Figure 3:
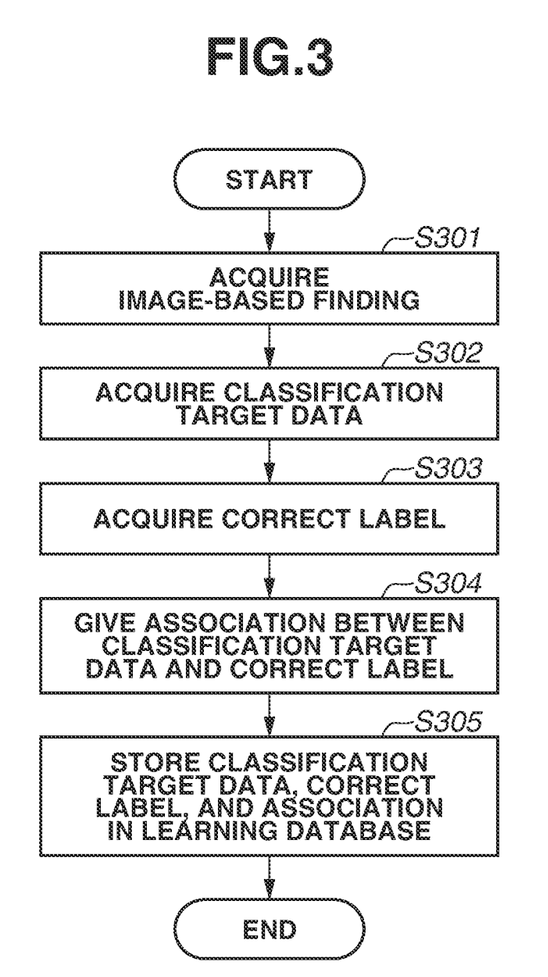
FIG. 3 is a flowchart illustrating an example of processing for creating learning data.

The learning data according to the first exemplary embodiment is created in accordance with a flowchart illustrated in FIG. 3. In the following description, all the image-based findings included in the radiographic interpretation reports stored in the medical information database 200 are listed and can be accessed sequentially.

In step S301, the learning data creation unit 102 acquires the first image-based finding from the list. When the subsequent image-based findings are accessed, the learning data creation unit 102 acquires the second image-based finding from the list first and the subsequent findings sequentially.

In step S302, the learning data creation unit 102 acquires classification target data. In the first exemplary embodiment, the classification target data is a lesion image. The lesion image is an image obtained by automatically extracting a region whose center position overlaps with the center position of an ROI and whose size is twice the ROI from a medical image. The lesion image may be two-dimensional pixel data or three-dimensional voxel data. The lesion image may be previously extracted at the time of registration in medical information. Alternatively, instead of extracting the lesion portion, an image including an ROI may directly be used as the lesion image.

In step S303, the learning data creation unit 102 acquires a correct label. In the first exemplary embodiment, the correct label is a diagnostic name. The diagnostic name is automatically selected from the definitive diagnoses included in an electronic health record having the same patient ID as that of the radiographic interpretation report including the image-based finding acquired in step S301. More specifically, the diagnosis whose creation date and time is later than and the closest to the radiographic interpretation report is used. A pathological report may be stored in advance in the medical information database 200, and a definitive diagnosis created immediately after the pathological report may be used. If the definitive diagnosis concerned does not exist, a corresponding image-based diagnosis may be used. In this case, when the definitive diagnosis concerned is created, the image-based diagnosis is replaced with the created definitive diagnosis.

In step S304, the learning data creation unit 103 dives an association between the classification target data acquired in step S302 and the correct label acquired in step S303. Information about The association may be given manually by a doctor or may be given automatically. For example, from the relationship between a medical image and an image-based diagnosis included in the radiographic interpretation report, the association between the classification target data and the definitive diagnosis may be obtained by analogy and given to the information.

In step S305, the learning data creation unit 102 stores in a set with the classification target data acquired in step S302, the correct label acquired in step S303, and the association given in step S304 in the learning database 300. In step S305, the learning data creation unit 102 stores information about the creators of the classification target data, the correct label, and the association therebetween in the learning database 300. When the items in learning data (for example, the classification target data, the correct label, and in addition the association therebetween) are created automatically, information indicating "AI" is stored as the information about the creators. Further, when an item is acquired from an electronic health record, information about the creator of the acquired item is stored. When an item is acquired from a radiographic interpretation report, information about the creator of the radiographic interpretation report is stored.

Configuration of Learning Data

Figure 4A:
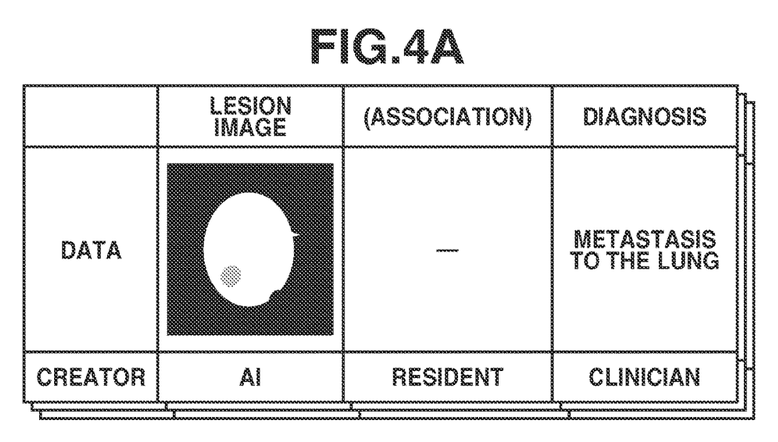
FIGS. 4A to 4C illustrate examples of a configuration of learning data.
Figure 4B:
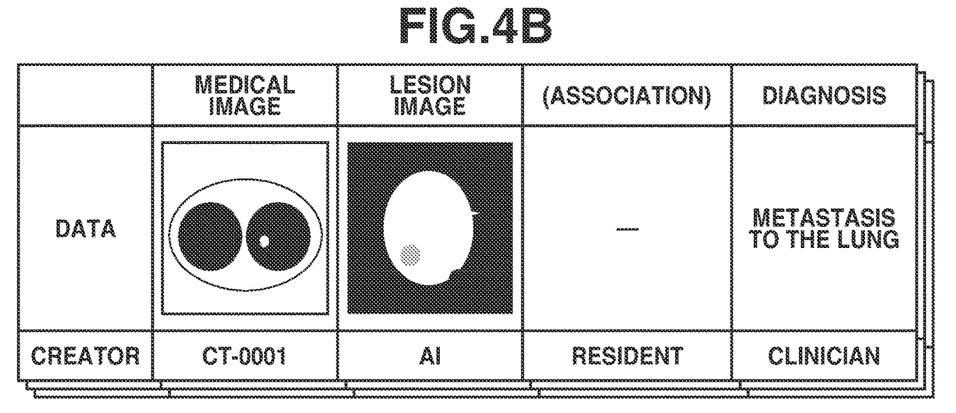
Figure 4C:
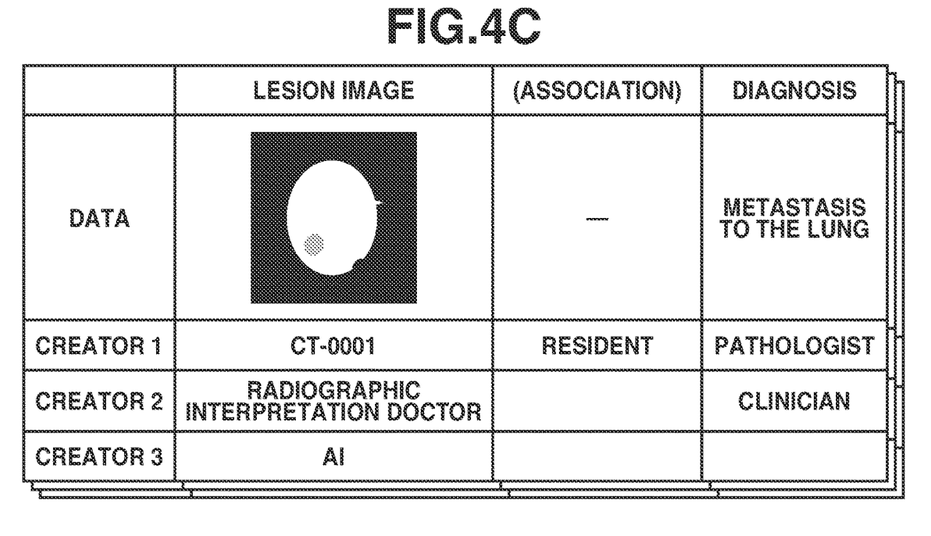

FIGS. 4A to 4C illustrate examples of learning data according to the first exemplary embodiment. In the examples in FIGS. 4A to 4C, an individual lesion image is automatically extracted from a medical image on the basis of ROI information given by a radiographic interpretation doctor. Information registered in an electronic health record is used for the diagnosis. In addition, association between a lesion image and a diagnosis is given manually by a resident.

FIG. 4A illustrates an example in which only the information about the final creators of classification target data, a correct label, and association therebetween are stored. FIG. 4B illustrates an example in which the learning data is formed by broken-up items and information about the creators of the broken-up items is stored. FIG. 4C illustrates an example in which information about the creators is stored as a history per item of the learning data.

Individual names may be stored as the creators. Alternatively, job titles such as a clinician and a radiographic interpretation doctor may be stored as the creators. If a medical image is used, information about a modality that has generated the medical image by imaging, such as a type and a model number of the modality and the name of the manufacturer of the modality, may be stored in an item for the learning data. Further, if the lesion image is used, information about a computer that has generated the lesion image, such as a type and a model number of the computer and the name of the manufacturer of the computer, may be stored in an item for the learning data, in addition to information as used in the above case of the medical image.

Method for Calculating Reliability Level of Learning Data

Figure 5:
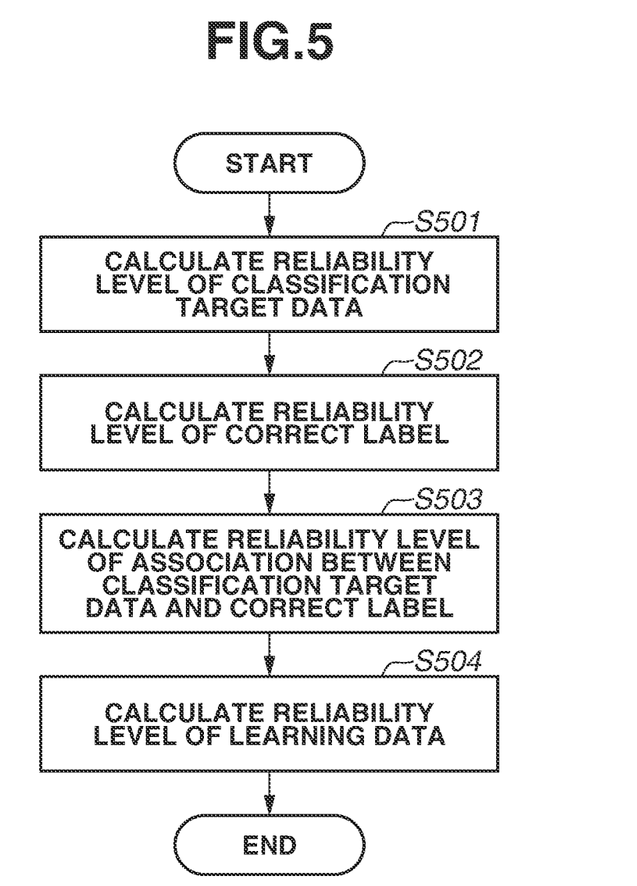
FIG. 5 is a flowchart illustrating an example of processing for calculating a reliability level of learning data.
Figure 6A:
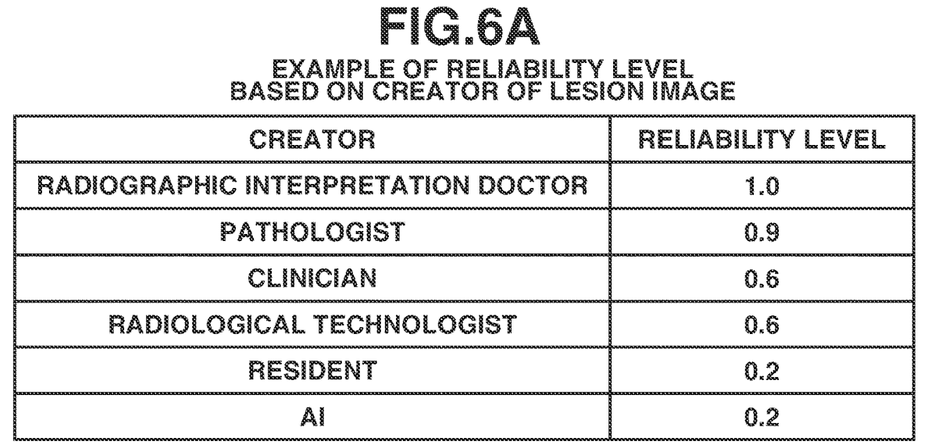
FIGS. 6A to 6C illustrate examples of reliability levels based on information about creators.
Figure 6B:
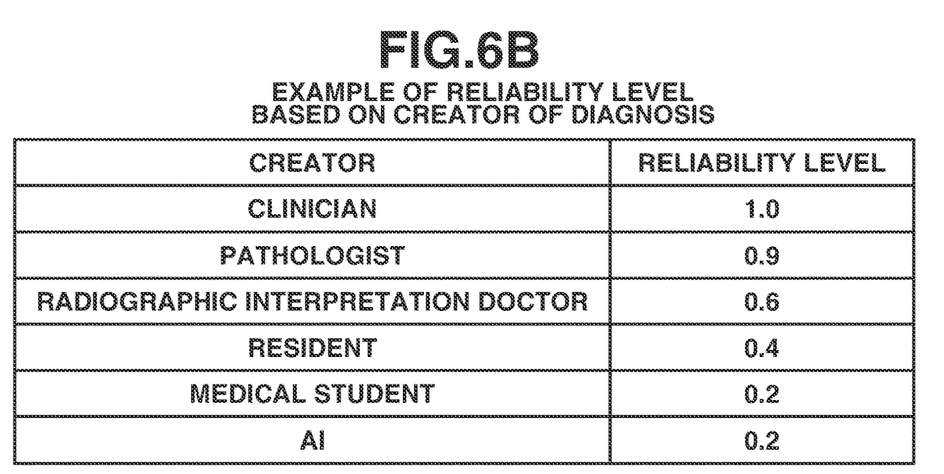
Figure 6C:
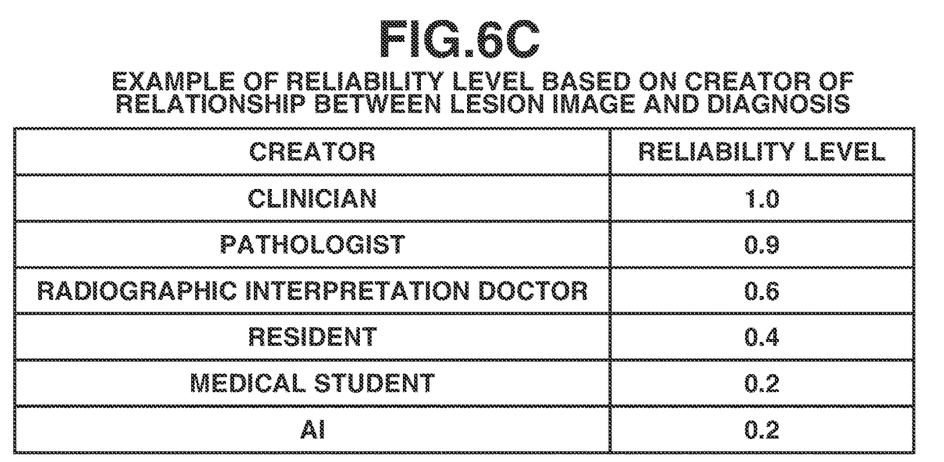

The reliability level of learning data is calculated in accordance with a flowchart illustrated in FIG. 5. In the following description, a reliability level based on information about a creator is determined in advance in a format illustrated in FIGS. 6A, 6B and 6C. More specifically, the reliability level is determined depending on whether the creator is AI or a person having a job title.

In step S501, the reliability level calculation unit 103 calculates a reliability level $R_{data}$ of classification target data. The reliability level $R_{data}$ is acquired from the table illustrated in FIGS. 6A, 6B and 6C on the basis of the type of the classification target data and information about the creator (information about the classification target data). In a case where the individual name is stored as a creator, the individual name is stored in such a manner that the job titles of the individual names can be acquired separately. Thus, after converting an individual name into a corresponding job title, the reliability level calculation unit calculates the reliability $R_{data}$. If the creator is unknown, the reliability level calculation unit 103 may estimate the job title of the creator from the system from which subject information has been acquired. For example, when a diagnosis is acquired from an electronic health record, the reliability level calculation unit 103 estimates that the creator of the diagnosis is a clinician. When a diagnosis is acquired from a pathological report, the reliability level calculation unit 103 estimates that the creator of the diagnosis is a pathologist.

In a case where classification target data includes a plurality of items as illustrated. In FIG. 4B or a history is stored as illustrated in FIG. 4C, weighted addition may be performed on the reliability levels based on the creators of the individual items, and the result of the calculation may be used as the reliability level of the classification target data. For example, the reliability level $R_{data}$ of the classification target data illustrated in FIG. 4B is calculated as indicated by equation 1, where a reliability level $R_{img}$ based on the creator of the medical image, a reliability level $R_{roi}$ based on the creator of the ROI, a reliability level $R_{les}$ based on the creator of the lesion image, and a weight $w_n$ per data are used.

$$R_{data}=w_1 \cdot R_{img}+W_2 \cdot R_{roi}+W_3 \cdot R_{les} \quad \text{(Equation 1)}$$

The weights can be set freely so that $\Sigma w_n=1$. In this case, for example, $w_1=0.1$, $w_2=0.5$, and $w_3=0.4$.

In step S502, the reliability level calculation unit 103 calculates a reliability level $R_{label}$ of the correct label. The reliability level $R_{label}$ is calculated in the same way as that used to calculate the reliability level $R_{data}$ in step S501 on the basis of information about a type of the correct label and the creator (information about the label.).

In step S503, the reliability level calculation unit 103 calculates a reliability level $R_{rel}$ of the association between the classification target data and the correct label. Namely, this processing corresponds to an example of an itemized reliability level calculation unit configured to calculate a third reliability level, which is reliability level of information about an association between a classification target data and a label. The reliability level $R_{rel}$ is calculated in the same way as that used to calculate the reliability level $R_{data}$ in step S501 on the basis of information about the creator of the association between the classification target data and the correct label.

In step S504, the reliability level calculation unit 103 performs weighted addition of the reliability levels calculated in steps S501 to S503, to calculate a reliability level $R_{tr}$ of the learning data. Namely, this processing corresponds to an example of a learning data reliability level calculation unit configured to calculate a learning data reliability level, which is a reliability level of learning data including a classification target data and a label, based on the first reliability level and the second reliability level. This processing also corresponds to an example of a learning data reliability level calculation unit configured to calculate a learning data reliability level on the basis of the third reliability level. The reliability level $R_{tr}$ is calculated as indicated by equation 2, which uses the reliability levels $R_{data}$, $R_{label}$, and $R_{rel}$ and the individual weights $w_n$.

$$R_{tr}=w_1 \cdot R_{data}+W_2 \cdot R_{label}+W_3 \cdot R_{rel} \quad \text{(Equation 2)}$$

The weights can be set freely so that $\Sigma w_n=1.0$. In this case, for example, $w_1=0.3$, $w_2=0.3$, and $w_3=0.4$.

The learning data reliability level $R_{tr}$ may be calculated as indicated by equation 3, which does not use the reliability level $R_{rel}$ of the association between the classification target data and the correct label.

$$R_{tr}=w_1 \cdot R_{data}+W_2 \cdot R_{label} \quad \text{(Equation 3)}$$

Method for Learning Classification Model

In the first exemplary embodiment, a general convolutional neural network (CNN) used as a classification model. The classification model is learned by performing mini batch learning. Namely, the classification model learning unit 104 acquires a small number of learning data as a mini batch from all the learning data and evaluates a classification model by using the mini batch data. The classification model learning unit 104 changes the weight of an individual node of the classification model on the basis of the evaluation result and evaluates the classification model by using another mini batch. By repeating this procedure, the classification model learning unit 104 increases the accuracy of the classification model.

In the first exemplary embodiment, the classification model learning unit 104 randomly selects a mini batch from all the learning data. In addition, the classification model learning unit 104 ends the learning when the product of the number of learning data included in the mini batch and the number of times of the repetition exceeds the total number of learning data. In this case, learning data that has never been included in the mini batch or learning data that has been redundantly included could exist.

Figure 7:
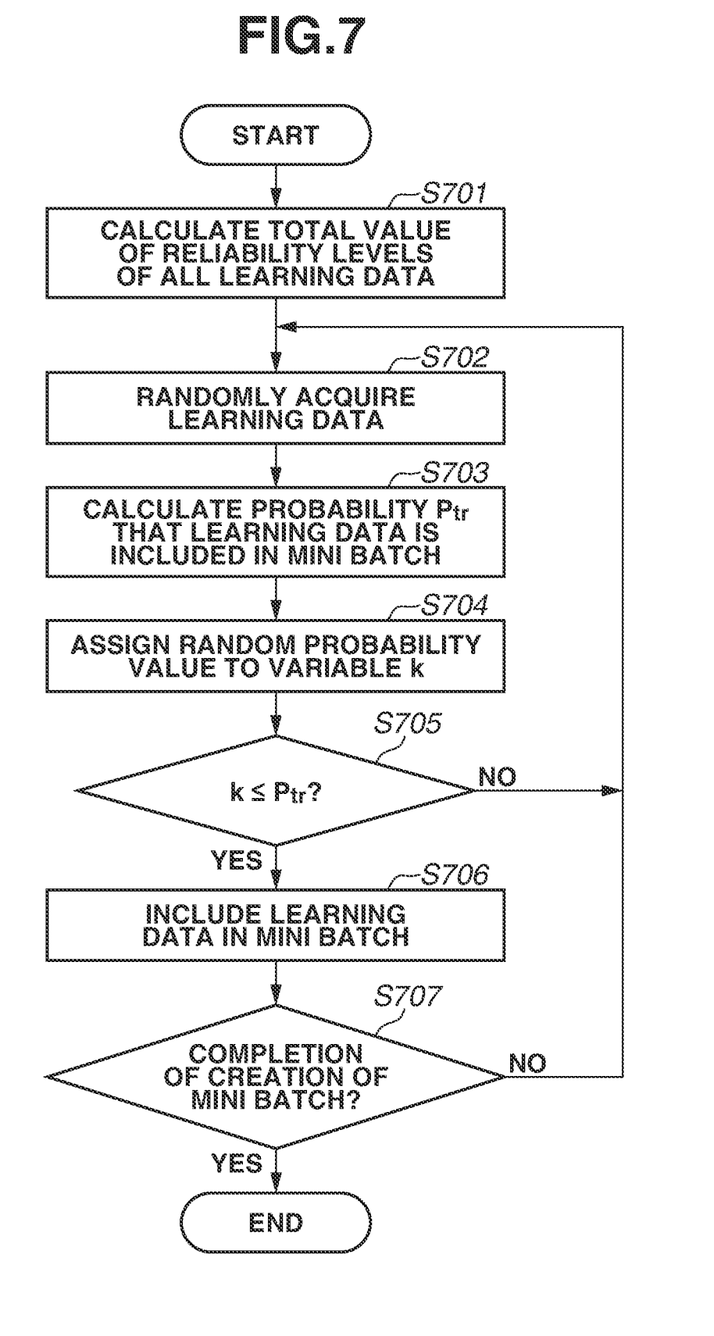
FIG. 7 is a flowchart illustrating an example of a learning data selection method.

Learning data in the mini batch is selected is accordance with a flowchart in FIG. 7.

In step S701, the classification model learning unit 104 calculates a total value $\Sigma R$ of reliability levels of all learning data.

In step S702, the classification model learning unit 104 randomly acquires one piece of learning data from all learning data.

In step S703, the classification model learning unit 104 calculates a probability $P_{tr}$ that the learning data acquired in step S702 is included in the mini batch. The probability $P_{tr}$ is calculated as indicated by equation 4, which uses the reliability level $R_{tr}$ of the learning data.

$$P_{tr} = \left(\frac{R_{tr}}{\Sigma R}\right) \cdot 100 \qquad \text{(Equation 4)}$$

In step S704, the classification model learning unit 104 randomly assigns one of the integers from among 1 to 100 to a variable k.

In step S705, the classification model learning unit 104 compares the variable k with the probability $P_{tr}$. If $k \leq P_{tr}$ (YES in step S705), the processing proceeds to step S706. Otherwise (NO in step S705), the processing returns to step S702.

In step S706, the classification model learning unit 104 includes the learning data acquired in step S702 in the mini batch.

In step S707, the classification model learning unit 104 determines whether the number of learning data included in the mini batch has exceeded a prescribed value. If exceeded (YES in step S707), the classification model learning unit 104 ends the present processing. Otherwise (NO in step S707), the processing returns to step S702.

Through the above processing, learning data having a higher reliability level is more likely to be included in the mini batch. The learning method is not limited to the above method. A different method may be used as long as The impact on the learning can be adjusted on the basis of the learning data reliability level. For example, a method based on Adaboost described in Japanese Patent Application Laid-Open No. 2009-282686 may be used.

When the learning is performed based on a CNN, diagnostic names (correct labels) of the same kind are collected and converted into numerical values representing the respective diagnoses. The number of diagnoses to be classified may be determined in advance or dynamically determined on the basis of the diagnoses included in the learning data.

Thus, the first exemplar; embodiment relates to learning performed by a classifier for classifying lesion images into predetermined types of diagnoses. According to the first exemplary embodiment, the reliability levels of each item included in learning data are evaluated, and the reliability level the learning data is evaluated by integrating the reliability levels. By changing the impact on the learning on the basis of these reliability levels, even when plural pieces of learning data with different qualities coexist, accurate learning can be performed.

Variation of First Exemplary Embodiment

While the reliability level of learning data is calculated on the basis of information about the creators of the items constituting the learning data in the first exemplary embodiment, a different method may be used.

For example, when a creator is a doctor, the reliability level calculation unit 103 may calculate the reliability level on the basis of more specific information, such as the accuracy of diagnosis in medical examination or the years of experience. In this way, the reliability level of learning data can be changed on the basis of the ability of the doctor who has been involved in creation of the learning data.

In addition, for example, the reliability level calculation unit 103 may adjust the reliability level on the basis of the source (provider) from which the medical information has been acquired, such as a public database or an in-hospital system, instead of the creators of the data. Thus, the reliability level of learning data can be changed on the basis of the quality of the source database from which the medical information has been acquired.

In addition, for example, the reliability level calculation unit 103 may adjust the reliability level according to a temporal relationship with other information such as the diagnosis in the electronic health record written after a pathological test. In this way, the reliability level of learning data can be changed on the basis of the amount or quality of information used as a basis for the diagnosis.

In addition, for example, the reliability level calculation unit 103 may calculate the reliability level on the basis of the amount of source data information such as the number of pixels in a medical image or a slice thickness. In this way, the reliability level of learning data can be changed on the basis of the amount or quality of information used as a basis for the diagnosis.

In addition, for example, the reliability level calculation unit 103 may calculate the reliability level on the basis of the existence or the type of a standard relating to the data creation, such as whether a criterion for the diagnosis is clarified. thus, the reliability level of learning data based on information created in accordance with a standard can be made higher than other learning data. Namely, this is an example of an itemized reliability level calculation unit configured to calculate, based on information about a creation or acquisition method of items constituting the learning data, the first reliability level or the second reliability level of the respective items.

In addition, for example, the reliability level calculation unit 103 may calculate the reliability level on the basis of information about patterns that can be employed when the learning data is created, such as the number of candidates of the correct labels that could be associated with the classification target data. Thus, the reliability level of learning data can be changed on the basis of the difficulty of the data creation.

Next, a second exemplary embodiment will be described. An information processing apparatus according to the second exemplary embodiment formulates a classifier for classifying lesion images into a predetermined type of findings names. The information processing apparatus formulates a classifier through machine learning that employs learning data which use lesion images as classification target data and the findings names as correct labels. Hereinafter, only the difference from the information processing apparatus according to the first exemplary embodiment will be described.

Similar to the first exemplary embodiment, the learning data according to the second exemplary embodiment is created in accordance with the flowchart illustrated in FIG. 3. However, unlike the first exemplary embodiment in which a correct label is acquired in step S303, a findings name is acquired in step S303. The findings name is acquired from the information about the image-based findings acquired in step S301. The findings name indicates characteristics of the lesion portion, and the classification of the findings name differs depending on the types of The characteristics. The exemplary types of the characteristics of the lesion portion are a shape, a concentration, etc. Different learning data and a different classifier are obtained depending on the target characteristics.

Thus, the second exemplary embodiment relates to formulation of a classifier for classifying lesion images into predetermined types of findings names. According to the second exemplary embodiment, the reliability levels of the individual items included in learning data are evaluated, and the reliability level of the learning data is evaluated by integrating the reliability levels. By changing the impact on the learning on the basis of these reliability levels, even when plural pieces of learning data of different qualities coexist, accurate learning can be performed.

Other Embodiments

In the above exemplary embodiments, a lesion image is used as the classification target data. However, the present invention is not limited to this example. For example, pathological images obtained from pathological tests may be used as the classification target data, and a classifier that classifies pathological images into a plurality of diagnoses may be formulated.

In addition, description of symptoms in electronic health records, vital data such as body temperatures and blood pressures, and blood test results may be used as the classification target data, and a classifier that classifies these items of information into a plurality of diagnoses may be formulated. In this case, instead of the CNN, a general deep neural network (DNN) is used as a classification model.

In the above exemplary embodiments, the present invention has been applied to the field of medicine. However, the application of the present invention is not limited to the field of medicine. For example, the present invention is effective when a high level of expertise or technology is needed to create classification target data or labels. For example, the present invention is effective in estimating emotion from the facial expression or voice of a person, estimating failure from small variation of a machine, or estimating illness from small variation of a crop.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-167258, filed Aug. 31, 2017, which is hereby incorporated by reference herein in its entirety.

What is claimed is:

1. An information processing apparatus comprising:
one or more processors; and
at least one memory storing instructions executable by the one or more processors to perform operations comprising:
calculating a first reliability level, wherein the first reliability level is a reliability level of classification target data, and a second reliability level, wherein the second reliability level is a reliability level of a label associated with the classification target data, and wherein the first reliability level and the second reliability level are different from each other;
calculating a learning data reliability level of learning data including the classification target data and the label based on the first reliability level and the second reliability level; and
formulating a classification model for giving a label to desired classification target data based on plural pieces of learning data and learning data reliability levels.

2. The information processing apparatus according to claim 1, the operations further comprising:
calculating a third reliability level, wherein the third reliability level is a reliability level of information about an association between the classification target data and the label; and
calculating the learning data reliability level based on the third reliability level.

3. The information processing apparatus according to claim 1, wherein the calculating the first reliability level comprises calculating the first reliability level of the classification target data based on information about the classification target data included in the learning data.

4. The information processing apparatus according to claim 3, wherein the information about the classification target data includes information about a creator or a provider of the classification target data included in the learning data.

5. The information processing apparatus according to claim 1, wherein the calculating the second reliability level comprises calculating the second reliability level of the label based on information about the label included in the learning data.

6. The information processing apparatus according to claim 5, wherein the information about the label includes information about a creator or a provider of the label included in the learning data.

7. The information processing apparatus according to claim 1, wherein the calculating the first reliability level and the second reliability level comprises calculating, based on information about a creation or acquisition method of respective items included in the learning data, the first reliability level or the second reliability level of the items.

8. An information processing method comprising:
calculating a first reliability level, wherein the first reliability level is a reliability level of classification target data, and a second reliability level, wherein the second reliability level is a reliability level of a label associated with the classification target data, and wherein the first reliability level and the second reliability level are different from each other;

calculating a learning data reliability level of learning data including the classification target data and the label based on the first reliability level and the second reliability level; and formulating a classification model for giving a label to desired classification target data based on plural pieces of learning data and learning data reliability levels.

9. An information processing system comprising:

one or more processors; and at least one memory storing instructions executable by the one or more processors to perform operations comprising:

calculating a first reliability level, wherein the first reliability level is a reliability level of classification target data, and a second reliability level, wherein the second reliability level is a reliability level of a label associated with the classification target data, and wherein the first reliability level and the second reliability level are different from each other;

calculating a learning data reliability level of learning data including the classification target data and the label based on the first reliability level and the second reliability level; and formulating a classification model for giving a label to desired classification target data based on plural pieces of learning data and learning data reliability levels.

* * * * *